(12) United States Patent
Griffin et al.

(10) Patent No.: US 11,975,417 B2
(45) Date of Patent: May 7, 2024

(54) CHAMFERING OPTICAL FIBER

(71) Applicant: Cyclone Biosciences, LLC, Phoenix, AZ (US)

(72) Inventors: Stephen E. Griffin, Peoria, AZ (US); Brian Barr, Scottsdale, AZ (US)

(73) Assignee: CYCLONE BIOSCIENCES, LLC, Phoenix, AZ (US)

( * ) Notice: Subject to any disclaimer, the term of this patent is extended or adjusted under 35 U.S.C. 154(b) by 339 days.

(21) Appl. No.: 17/385,606

(22) Filed: Jul. 26, 2021

(65) Prior Publication Data
US 2021/0362286 A1    Nov. 25, 2021

Related U.S. Application Data

(63) Continuation-in-part of application No. 15/426,117, filed on Feb. 7, 2017, now Pat. No. 11,097,395.

(51) Int. Cl.
| | |
|---|---|
| *B24B 19/22* | (2006.01) |
| *A61B 18/22* | (2006.01) |
| *B24B 9/08* | (2006.01) |
| *B24B 41/00* | (2006.01) |
| *G02B 6/25* | (2006.01) |
| *G02B 6/26* | (2006.01) |

(52) U.S. Cl.
CPC ............ *B24B 19/226* (2013.01); *A61B 18/22* (2013.01); *B24B 9/08* (2013.01); *B24B 41/002* (2013.01); *B24B 41/005* (2013.01); *G02B 6/25* (2013.01); *G02B 6/262* (2013.01)

(58) Field of Classification Search
CPC ..... B24B 19/226; B24B 19/14; B24B 31/064; B24B 31/06; B24B 31/062; B24B 31/067; B24B 31/073; G02B 6/3863; G02B 6/25; G02B 6/262
See application file for complete search history.

(56) References Cited

U.S. PATENT DOCUMENTS

| | | | | |
|---|---|---|---|---|
| 3,975,865 | A | | 8/1976 | Lewis |
| 3,999,837 | A | * | 12/1976 | Bowen ................. G02B 6/3825 385/62 |
| 4,850,664 | A | * | 7/1989 | Iri .......................... B24B 19/226 385/85 |
| 5,123,219 | A | * | 6/1992 | Beard ................... B24B 19/226 451/49 |
| 5,218,786 | A | * | 6/1993 | Takahashi ............. B24B 19/226 451/276 |
| 5,291,570 | A | | 3/1994 | Filgas et al. |
| 5,412,747 | A | * | 5/1995 | Matsuoka ............. B24B 19/226 385/139 |

(Continued)

*Primary Examiner* — Joel D Crandall
(74) *Attorney, Agent, or Firm* — Quarles & Brady LLP; Yakov S. Sidorin

(57) ABSTRACT

A tool for chamfering cleaved tips of optical fibers. The tool including conical bores of relatively smooth and hard material terminate at a cylindrical bore that is slightly larger than the fiber core maximum diameter and a fiber centering bore that is slightly larger than the fiber coating maximum diameter. The tool provided such that when a cleaved fiber tip is inserted into the centering bore the sharp edge falls upon the chamfering surface that, when rotated relative to the fiber, gently grinds the edge to the chamfer angle. Chamfering cannot occur on the core face due to the absence of tool surface at this dimension.

13 Claims, 8 Drawing Sheets

(56) References Cited

U.S. PATENT DOCUMENTS

| | | | |
|---|---|---|---|
| 5,615,291 A | 3/1997 | Hayakawa et al. | |
| 7,419,308 B2 * | 9/2008 | Ma | G02B 6/25 |
| | | | 385/115 |
| 9,235,004 B2 | 1/2016 | Bansal et al. | |
| 2003/0174974 A1 * | 9/2003 | Yasuda | G02B 6/3857 |
| | | | 385/80 |
| 2004/0161205 A1 * | 8/2004 | Hengelmolen | G02B 6/3834 |
| | | | 385/78 |
| 2006/0105684 A1 * | 5/2006 | Lurie | B24B 19/226 |
| | | | 451/41 |
| 2006/0269192 A1 * | 11/2006 | Hayasaka | G02B 6/3834 |
| | | | 385/60 |
| 2008/0031573 A1 * | 2/2008 | Droege | G02B 6/3861 |
| | | | 385/78 |
| 2008/0195085 A1 | 8/2008 | Loeb | |
| 2011/0015756 A1 | 1/2011 | Pawar et al. | |
| 2011/0075973 A1 | 3/2011 | Dean, Jr. et al. | |
| 2012/0070115 A1 | 3/2012 | Langseth et al. | |
| 2013/0089294 A1 * | 4/2013 | Zimmel | G02B 6/3861 |
| | | | 156/247 |
| 2013/0336618 A1 | 12/2013 | Danley et al. | |
| 2014/0321812 A1 * | 10/2014 | Bauco | G02B 6/3861 |
| | | | 29/461 |

* cited by examiner

Towards a rotor configured to rotate about 28

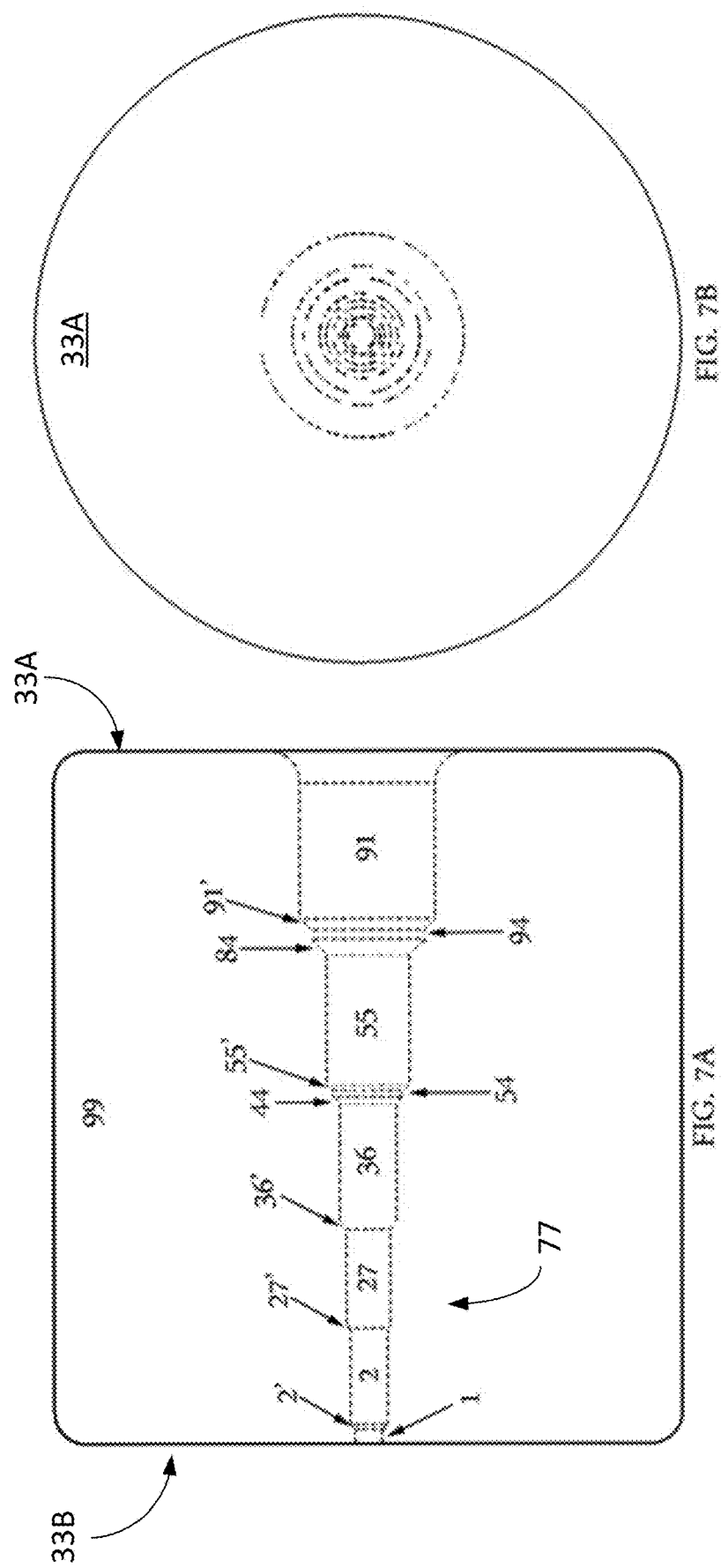

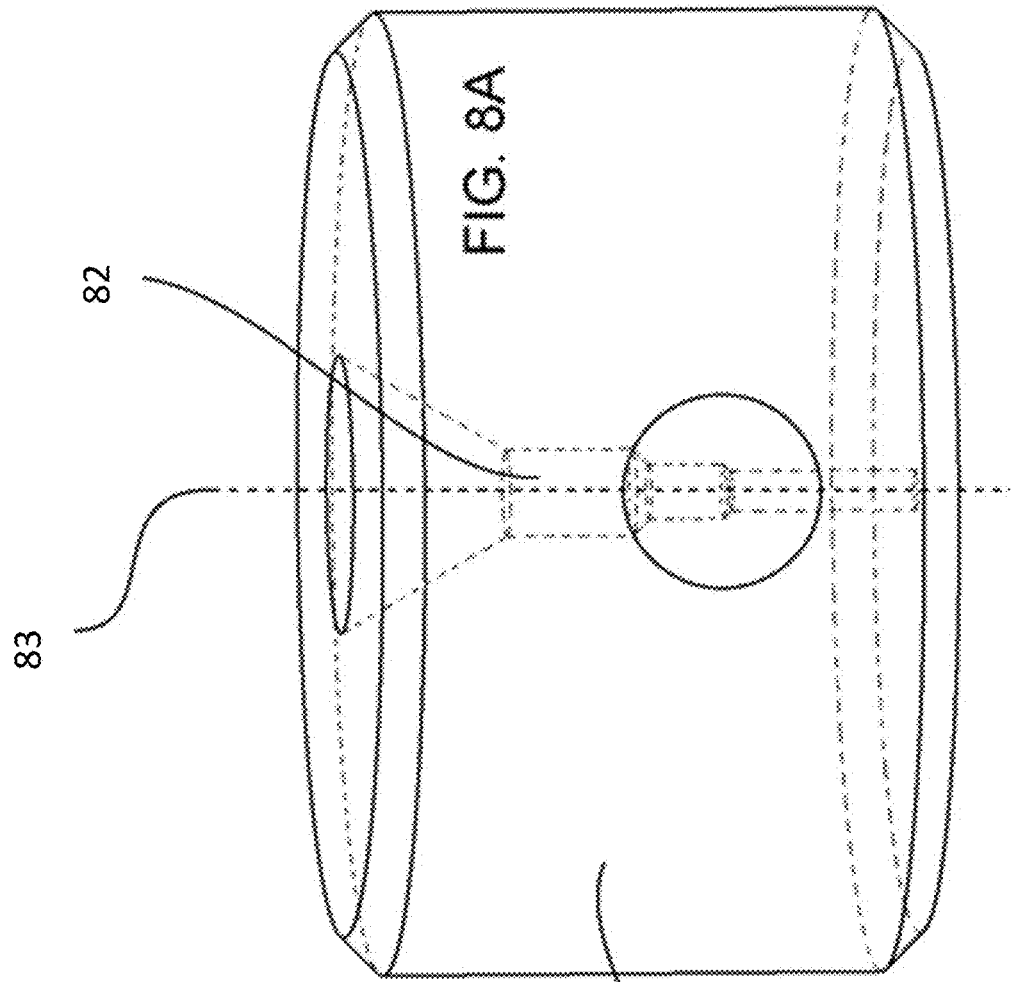
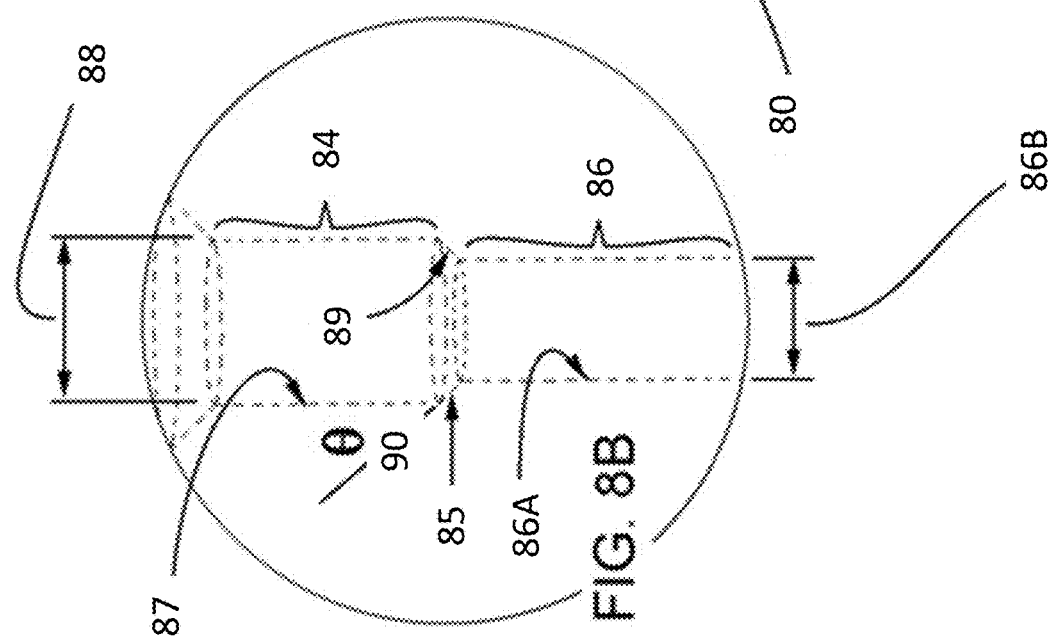

CHAMFERING OPTICAL FIBER

CROSS-REFERENCE TO RELATED APPLICATIONS

This patent application is a continuation-in-part from the U.S. patent application Ser. No. 15/426,117 now published as US 2018/0222005, which was filed on Feb. 7, 2017, the disclosure of which is incorporated herein by reference.

TECHNICAL FIELD

This disclosure is directed to systems and methods configured to intraoperatively remove sharp glass edges from an endoscopic optical fiber while not modifying the spatial distribution of light emanating from the cleaved end of such fiber.

RELATED ART

Damaged endoscope working channel liners trigger more trips to there pair shop than any other wear and tear for these minimally invasive access instruments. "Bare" laser surgical fibers often have rounded edges when new (e.g. by laser polishing or by having ball lens tips). Reprocessing used surgical fibers requires stripping the protective jacket (also known as buffer), scoring the fiber, and cleaving to produce a new, flat output edge surface. When used for surgery conducted via endoscope access, such reprocessed fibers hang up within the hollow of the endoscope and can easily damage working channel liners by gouging, pitting, and occasionally perforating these polymer liners.

Practice shows that in some surgical procedures (e.g., during the laser lithotripsy) the tip of the surgical fiber rapidly 'burns back', which reduces the efficiency of laser energy delivery efficiency of the surgical device by as much as 50%. To recover the operational characteristics and desired performance of the so-burnt surgical fiber, the intraoperative (as opposed to the interoperative) reprocessing of the fiber is required, which currently is most commonly carried out with the use of sterile strippers and cleavers.

Chamfering the edges of a freshly cut laser surgical fiber, even outside of the surgical suite, is not a simple task. A typical surgical fiber includes an extremely hard (5.5 to 6.5 Mohs hardness) fused silica core ranging from 200 μm to 910 μm in diameter, and a very thin glass cladding layer (14 μm to 45 μm thick, often made of fluorine-doped fused silica). The resulting chamfering area (or, simply, a chamfer) must be confined to this cladding layer to prevent spatial distortion of the optical output from the fiber. Notably, any distortion of the fiber output (caused by, for example, by a chamfer extending into the core) renders a reprocessed fiber noncompliant with FDA requirements. Practice provide evidence that these requirements remain unmet by many (if not the majority) of reprocessed surgical fibers.

An example of chamfering a fiber is disclosed in U.S. Pat. No. 9,235,004 issued to Bansal, et al., which discusses a method for cleaving and chamfering an optical fiber that involves forming an opening (a window) in the fiber coatings with laser light, scribing the bare fiber within the bounds of this opening, applying tension to the fiber to cleave it, and then "chamfering" the cleaved end " . . . by applying heat from one of $CO_2$ laser, a plasma arc, a gas flame and a resistive coil. FIG. 2 of this patent depicts a filleted fiber tip, the filter of which extends well into the fiber core and is reproduced in the current disclosure as FIG. 6A.

SUMMARY

Embodiments of the invention address a persisting need in flexibility of forming a bevel or chamfer on a cleaved end of an optical fiber while not beveling or chamfering the optical fiber core (to maintain and/or preserve the spatial characteristics of light emanating from the cleaved end) by providing a chamfering tool configured to do so without requiring the optical fiber's distal end to be free. When used for chamfering the surgical optical fibers (such as well-defined endoscopic fibers), the proposed embodiments allow the user to achieve the desired goal intraoperatively, that is substantially during the surgical procedure. In a preferred form, the tool is configured for hand use.

Embodiments of the die of the tool include conical bores of relatively smooth and hard material terminate at a cylindrical bore (that is slightly larger than the fiber core maximum diameter) and a fiber centering bore (that is slightly larger than the fiber coating maximum diameter). When a cleaved fiber tip to-be-chamfered is inserted into the centering bore, the sharp edge falls upon the chamfering (substantially conical) surface that, when rotated relative to the fiber, gently grinds the edge to the chamfer angle. Chamfering cannot occur on the core face due to the absence of tool surface at this dimension.

To this end, embodiments of the invention provide a tool for chamfering an optical fiber, which tool includes a die with a bore within the die and a housing body shaped as a bar having distal and proximal ends, a second axis, and an axial recess.

The die is dimensioned to generally have the first diameter to be larger than the glass cladding diameter, the second diameter is smaller than the glass cladding diameter and larger than the glass core diameter.

The bore has a first axis, a first cylindrical portion with a first diameter, a second cylindrical portion having a second diameter that is smaller than the first diameter, and a first conical portion including a first base that has the first diameter and a second base that has the second diameter, said first conical portion connecting the first and second cylindrical portions. Generally, and substantially in any implementation of the tool, a surface of the first conical portion may be structured to possess at least one of a first hardness (that is greater than a second hardness of a glass material) and a first averaged surface roughness (that is greater than a second averaged surface roughness of a surface of any of the first and second cylindrical surfaces. When this is the case, the first hardness may be chosen to be at least 20 GPa and/or the surface of the first conical portion may be coated with a coating that has the at least one of the first hardness and the first averaged roughness. The axial recess is dimensioned to fixate at least a portion of the body therein when the first and second axes substantially coincide. In substantially any implementation, the axial recess is formed at the distal end with an open end of the recess facing away from the proximal end. The housing body generally includes a distal portion (in one implementation—with a knurled outer surface) and a proximal portion axially connected to the distal portion and having a terminus dimensioned to have a larger first cross-sectional dimension than a second cross-sectional dimension of the proximal portion (here, the first and second cross-sectional dimensions are defined in a plane transverse to the first axis.) In the latter case, the tool may be configured to satisfy at least one of the following conditions: —the housing body includes a handle portion extending along the second axis and coupling the proximal portion to the distal portion, and an outer surface of the terminus is a convex surface.

Optionally, the housing may be configured as part of or be connected to a rotor of a motor assembly to be rotated about the second axis when the motor assembly is in operation.

Alternatively or in addition, a cross-section of the axial recess that is transverse to the second axis may be configured to have a substantially elliptical perimeter and/or a wall of the recess having the cross-section contains a recess thread that is reciprocal to a thread carried by the body on the substantially cylindrical outer surface. Alternatively or in addition—and in substantially any implementation, the tool may be configured to satisfy at least one of the following conditions: —the die has an outer surface dimensioned as elliptic cylindrical surface; —such outer surface of the die is rotationally-symmetric about the first axis; —such outer surface of the die carries a thread thereon; —the axial recess is axially-symmetric about the first axis; and—the axial recess is dimensioned to fixate said at least a portion of the die therein removably. In at least one embodiment, the tool includes a fastener cooperated with the housing body at the distal end and configured to affix the die in the axial recess while the first and second axes substantially coincide and/or the bore extends throughout the die to provide a fluid communication between a first portion of an ambient space next to a first surface of the die and a second portion of the ambient space next to a second surface of the body. (In the latter case, each of the first and second surfaces of the die is defined transverse the first axis.) In at least one implementation, the bore may be structured to additionally include a second conical portion including a third base that has the second diameter and a fourth base that has a third diameter that is smaller than the second diameter (such second conical connected to the second cylindrical portion). When the bore is so structured, the bore may additionally include a third cylindrical portion that is axially connected to the second conical portion and that has the third diameter.

BRIEF DESCRIPTION OF THE DRAWINGS

For a more complete understanding of the disclosure, reference should be made to the following detailed description and accompanying drawing figures, of which:

FIG. 2A depicts a related embodiment of a chamfering tool configured to chamfer a single fiber size for use in intraoperative fiber tip reprocessing with a chamfering die inserted, while

FIG. 5A is a side view of a blank aluminum cylindrical body of the die, FIG. 5B illustrates the cylindrical body after precision boring, FIG. 5C is an isometric view pf the body after the anodization process, and FIG. 5D illustrates the completed die in a partial cross-sectional view.

FIG. 6C provides additional details.

FIG. 7 shows is a side view (FIG. 7A) and top view (FIG. 7B) of a universal chamfering tool for optical fiber structured according to the idea of the invention.

FIG. 8 depicts a side view (FIG. 8A) of a chamfering tool and an expanded view (FIG. 8B) of the bore formed through the element of the embodiment of the chamfering tool.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another. While specific embodiments are illustrated in the figures with the understanding that the disclosure is intended to be illustrative, these specific embodiments are not intended to limit the scope of invention implementations of which are described and illustrated herein.

DETAILED DESCRIPTION

Embodiments of the invention solve the persisting problems and processing complications caused by the need in re-furbishing of the output end of the surgical optical fiber that has to be performed intraoperatively, that is during a particular surgical procedure, by providing a stand-alone tool configured for chamfering the optical fiber one end of which is attached to the console of the laser source (the light from which is delivered by the surgical fiber to the target area during the surgical procedure), causing the fiber to resist rotation about its axis. When implemented according to the idea of the invention, embodiments of the chamfering are judiciously structured not only to prevent the chamfer area from being extended into the fiber core (and confining the chamfer area to the glass cladding layer of the fiber, thereby preserving the intended spatial distribution of the output of light emanating from the terminal surface of the fiber) but also ensuring that the chamfering tool can be subjected to substantially any of the sterilization procedures recognized and/or used in related art.

Figure 1:
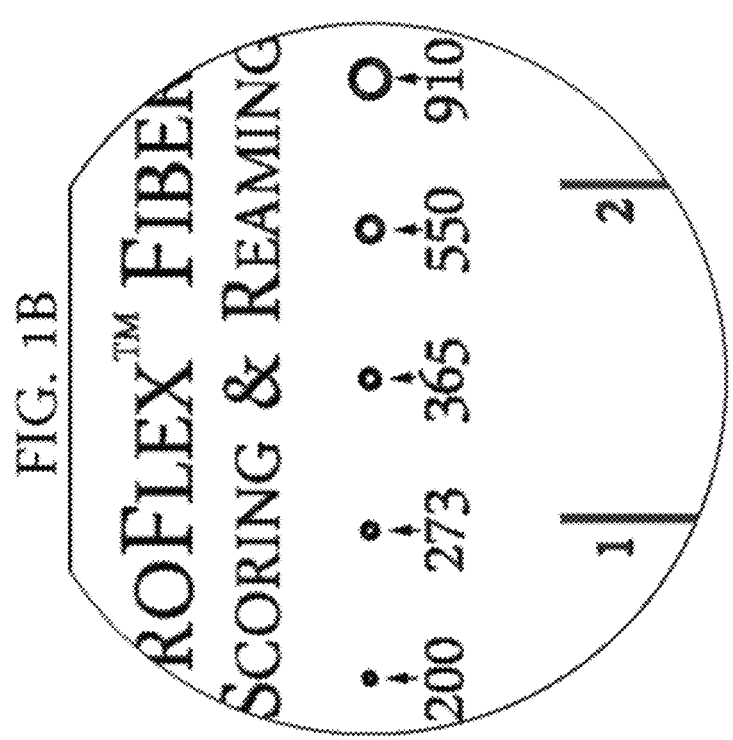
FIG. 1 depicts a modified fiber-scoring wafer, and includes FIG. 1A representing an embodiment of the invention in a top view with details shown in FIG. 1B, and FIG. 1C showing a cross-sectional view of the embodiment with details presented in FIG. 1D.
Figure 1:
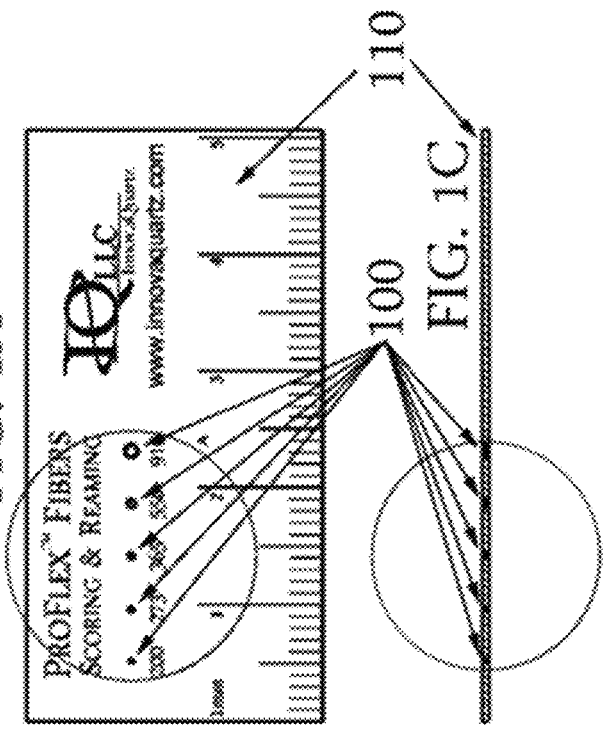
Figure 1:
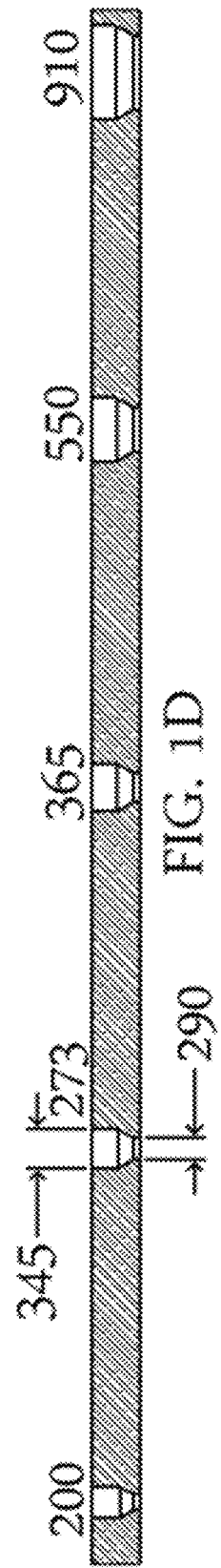

Fiber scoring wafers (aka cleaving tiles) are ubiquitous in the laser surgical marketplace. Logo-marked wafers are often used as promotional items at tradeshows and symposia. FIG. 1 illustrates an embodiment of a ceramic (for example, made from alumina) "two inch" scoring wafer 110 configured to chamfer laser surgical fibers and, in particular, fibers of standard sizes used in a laser lithotripsy procedure. The wafer is shown to be marked with a company logo, product name and slogan as well as a metric rule as a convenient reference in tip preparation. The depicted scoring wafer includes five chamfering holes, 100, which correspond to each of five standard (nominal) fiber core sizes, in microns: 200, 273, 365, 550 and 910. The maximum core, minimum cladding, and maximum coating dimensions of the standard laser lithotripsy optical fibers are summarized in Table 1. As the skilled person will readily appreciate, the minimum cladding thickness is not a function of the minimum cladding dimension and the maximum core dimension, but rather is a function of the minimum cladding-to-core diameter ratio and the minimum cladding diameter. (As such, the typical cladding thickness is offered for reference.) These dimensions are limiting for the embodiment of the chamfering tool.

TABLE 1

Critical Fiber Dimensions (millimeters)

| Fiber Core Max | Fiber Cladding Min | Fiber Coating Max | Clad Thickness |
|---|---|---|---|
| 0.208 | 0.235 | 0.278 | 0.020 |
| 0.283 | 0.294 | 0.335 | 0.014 |
| 0.373 | 0.392 | 0.438 | 0.018 |
| 0.562 | 0.590 | 0.640 | 0.025 |
| 0.940 | 0.985 | 1.050 | 0.040 |

FIG. 1A illustrates possible locations of the chamfering holes (bores) 100 on the wafer 110, while FIG. 1B provides a detailed view of the holes together with the hole size identifiers: 200, 273, 365, 550 and 910 that correspond to the five standard (nominal) fiber sizes. FIG. 1C provides a reference for the cross-sectional view of the chamfering holes presented in FIG. 1D where the hole sizes are again identified as 200 for the 200 µm diameter fiber hole, 273 for the 273 µm diameter fiber hole, 365 for the 365 µm diameter fiber hole, 550 for the 550 µm diameter fiber hole, and 910 for the 910 µm diameter fiber hole.

The most challenging fiber for chamfering is that with the 273 µm core; it has the thinnest cladding at 14 so the hole is chosen for illustrative dimensioning. The chamfer stop (substantially cylindrical) bore 290 for the 273 µm core fiber is approximately 285 µm to 290 µm in diameter or slightly larger than the largest possible fiber core produced within standard manufacturing tolerances. The fiber centering (substantially cylindrical) bore 345 for the 273 µm core fiber is approximately 340 µm to 345 µm in diameter or slightly larger than the diameter of such fiber's coating. These two bores 290, 345 are uninterruptingly joined along the corresponding axis by a conical chamfering surface (with an opening angle value preferably in the range from about 30° to about 120°).

To chamfer the target surgical fiber in the operating room, partial rotation of the fiber positioned in the chamfering hole about the fiber axis, reversal, and repetition can be sufficient but such a chamfering wafer may find more utility in interoperative reprocessing where fibers may be easily rotated relative to a stationary wafer. However, intraoperative reprocessing of the fiber with the wafer 100 depicted in FIG. 1 may prove more difficult, because fibers are typically attached to the laser console at one end and resist rotation.

Figure 2A:
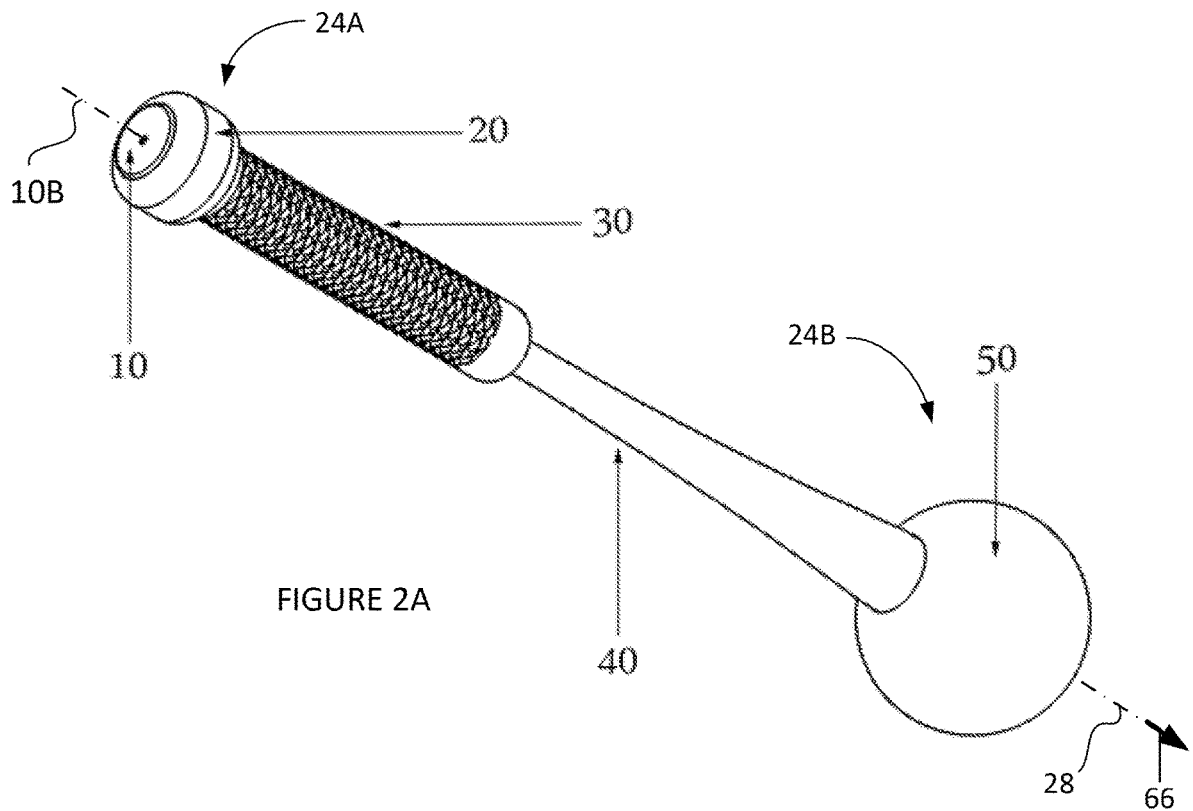
Figure 2B:
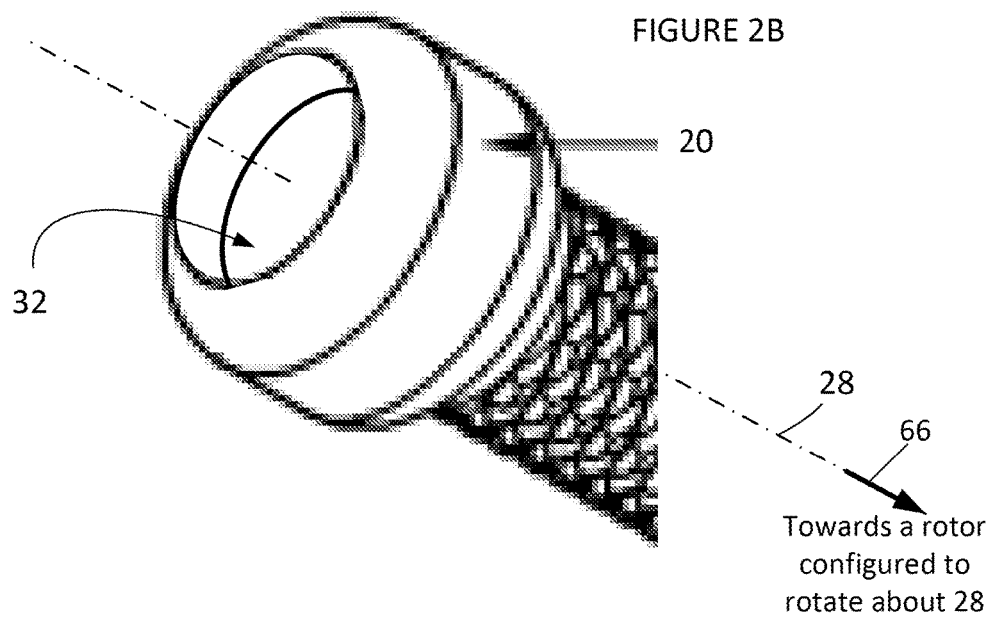
FIG. 2B illustrates a distal portion of the tool without the chamfering die.
Figure 3:
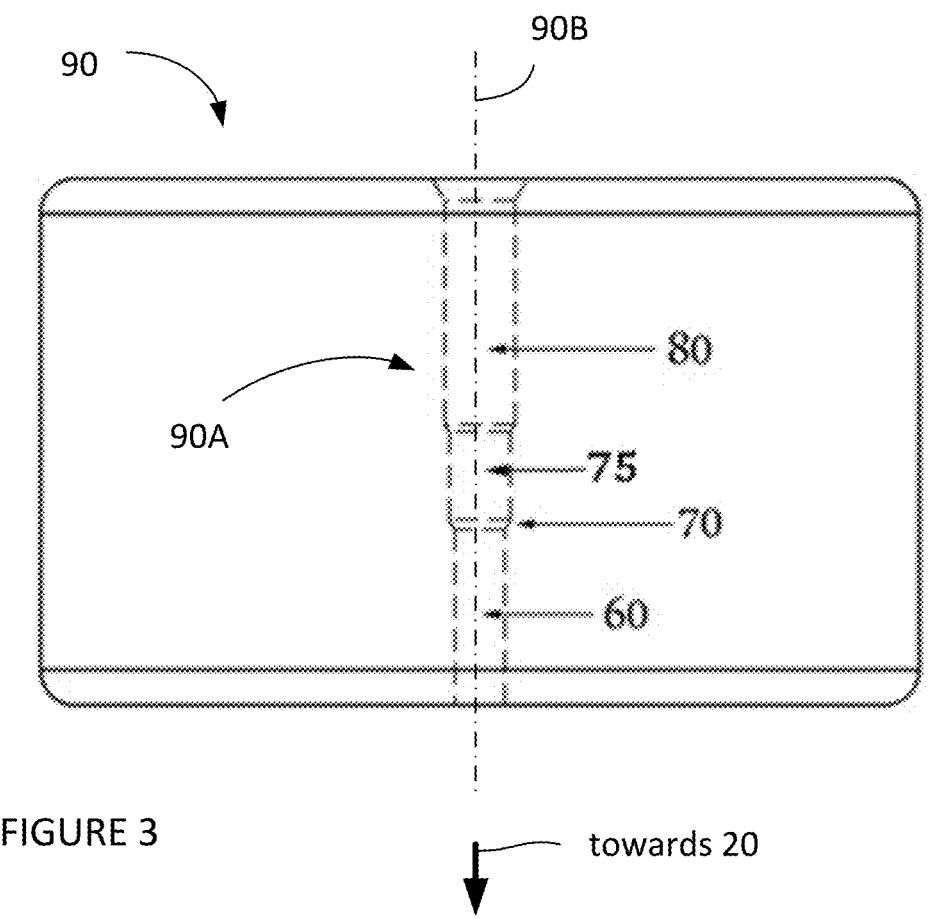
FIG. 3 presents details of a chamfering element (die) 10 of FIG. 2A in a cross-sectional side view.

For intraoperative fiber reprocessing, an embodiment of the chamfering tool may be preferred that is designed for a single-hand operation, that is a tool that can be easily cooperated with an end of the target fiber, and utilized with respect to such fiber end—all while being help with one hand. To this end, as illustrated in FIGS. 2A, 2B, and 3, an embodiment of the invention includes a chamfering body 10, 90 with a bore within the chamfering body. The bore has an axis 10B (also, 90B in FIG. 3), a first cylindrical portion with a first diameter, a second cylindrical portion with a second diameter that is smaller than the first diameter, and a first conical portion with a first base that has the first diameter and a second base that has the second diameter and with a predetermined opening angle. The wall of the first conical portion spatially uninterruptingly, without notches, connects the walls of the first and second cylindrical portions. The embodiment of the tool additionally includes a housing shaped generally as a bar or a rod (20, 30, 40, 50) and having a distal end 24A, a proximal end 24B, a second axis 28 along which the bar is extended, and an axial recess 32 that is dimensioned to house at least a portion of the body 10, 90 when the first axis of the body 10 and the second axis 28 of the housing substantially coincide. As shown in the specific case of FIG. 2A, the body 10 is almost completely inserted into and fixated in the axial recess of the housing. Generally, such axial recess is formed at the distal end 24A of the housing with an open end of the recess facing away from the proximal end 24B of the tool. The arrow 66 illustrates the optional operational coupling of the embodiment with a rotor (of a motor) that is configured to rotate about the axis 28, thereby causing the rotation of the housing with the die affixed therein to chamfer an end of the fiber inserted into a bore of the die.

In the specific implementation illustrated in FIGS. 2A, 2B, the distal portion 30 of the bar of the chamfering tool is knurled (to be able to rotated the tool about its axis with fingers when the tool is placed in a hand with the ball-shaped terminus 50 that is connected to the portion 30 via an extension handle 40. Generally, however, the cross-sectional dimension of the terminus at the proximal end of the housing element is made greater than the cross-sectional dimension of the majority of the housing element, and an outer surface of such terminus is preferably convex to minimize friction against the palm of the hand upon rotation of the tool with the fingers. Overall, the embodiment is dimensioned to fit in a palm of a hand of an average person when the terminus (for example, the ball 50) is settled at about a center of the palm while the distal portion is gripped with the two fingers (for example, between thumb and index finger, or between thumb and middle finger).

A centrosymmetric chamfering die 10 may be preferred. The die housing (20, 30, 40, 50) may be adapted for quick swapping between alternative dies (in which case the inner surface of the distal end 24A of the tool is dimensioned to removably accommodate multiple dies 10 of a standard dimension, akin to a structure of a screwdriver with a replaceable tip) to adapt the tool to fibers of different fiber sizes; alternatively—a separate tool may be provided for each of the standard fiber sizes. Mechanisms employed for sequential accommodation of dies (configured for chamfering differently-sized fibers) within the same housing (20, 30, 40 in this example) include mating threads carried on the inner surface of the recess in which a given die is placed at the end 20 of the housing and on the outer surface of such die (not shown for simplicity of illustration), and/or a fastener (not shown) cooperated with the housing at the distal end and configured to affix the die/body 10 in the axial recess 32 of the housing.

FIG. 3 depicts some details of one implementation 90 of a chamfering die 10, made from for example anodized aluminum, with a multi-section internal bore 90A and an axis 90B. The bore 90A includes a substantially cylindrical fiber guide bore portion 80 leading to the precise substantially-cylindrical fiber-coating accommodating bore portion 75 and a conical chamfering surface 70 at the end of the bore portion 75. The precise bore 60 is dimensioned to be slightly larger than the maximum value of the diameter of the target fiber's core and, therefore, is adapted to collect the fine silica dust produced during the chamfering operation. The most challenging fiber size of 273 µm core is accommodated by the bore 60 with internal diameter from about 285 µm to about 290 µm (or slightly larger than the largest possible fiber core that is produced within standard fiber manufacturing tolerances). The precision fiber centering bore portion 75 for such nominally-273 μm core diameter fiber is approximately 340 to μm 345 μm in diameter (or slightly larger than the fiber coating diameter). The fiber guide bore portion 80 can be approximately 400 μm in diameter.

In some cases, it may be desirable to limit the length of the precision fiber-centering bore portion 75 to reduce a portion of the target fiber that may incur coating damage to that very near the fiber's output surface. In practice, an approximately 0.5 mm to 1 mm long close-fitting centering bore 75 may be sufficient for ensuring the sharp edge of the cleaved fiber is properly positioned upon and in contact with the chamfer surface 70. (Indeed, approximately this length is typically burned bare of coating in production fibers, so failures due to factures from scratching is this short section of the target fiber should not increase the frequency or severity over historical levels.)

Figure 4:
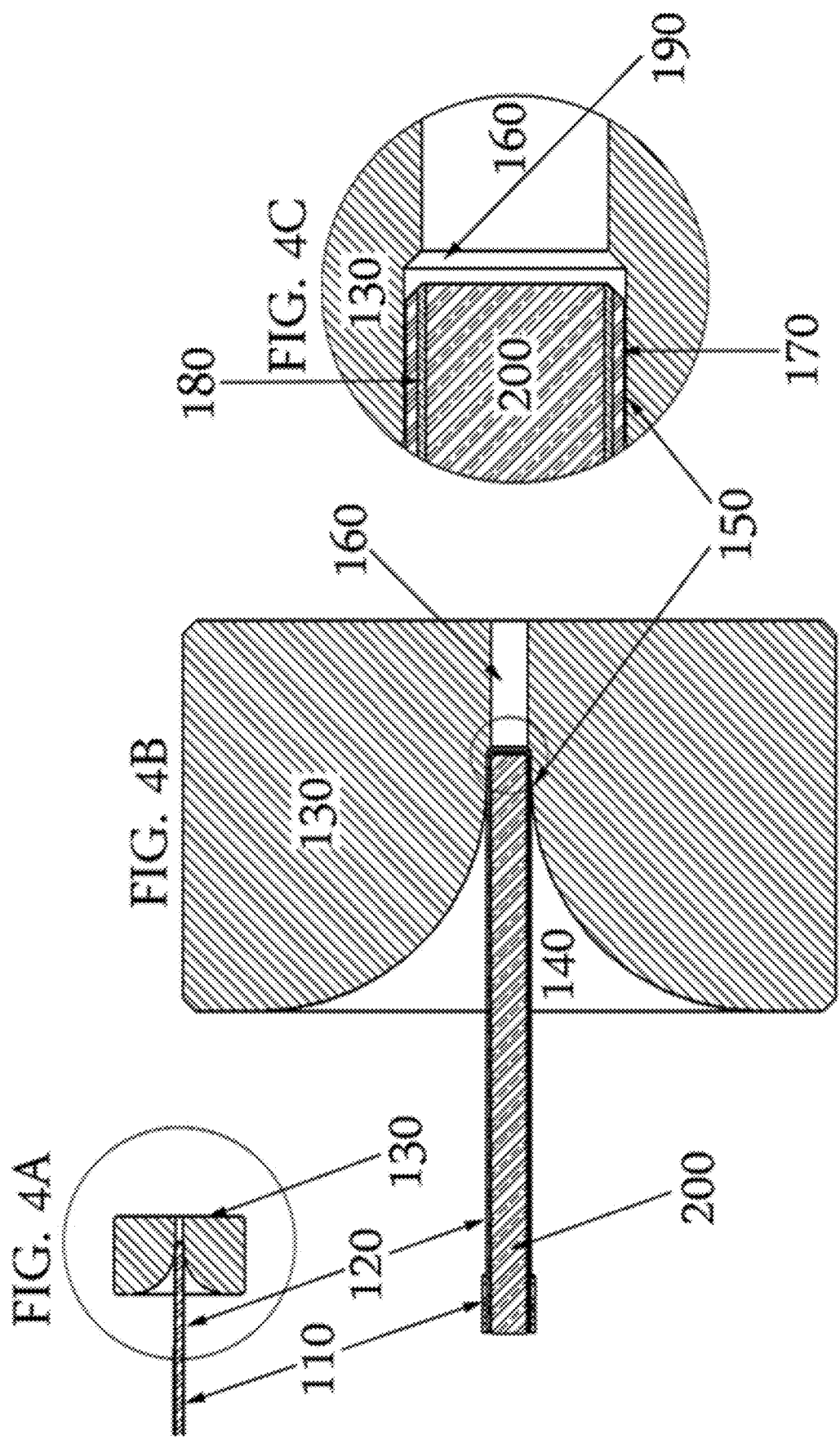
FIG. 4 (which includes FIGS. 4A, 4B, 4C) depicts a fiber inserted into an alternative embodiment of the tool of the invention, and provides some additional technical details.

FIG. 4 depicts a typical jacketed laser surgical fiber 110 (with a short-stripped section 120) that is inserted into a related embodiment 130 of the chamfering die 90 where the die 130 is a modified tungsten carbide wire drawing die with a classically filleted lead-in 140, see FIGS. 4A, 4B. Here, rather than terminate in a precision bore 160 (chosen to be slightly larger than the fiber core 200) as the standard wire-drawing die would do, a second bore 150 (that is slightly larger than the fiber coating 170 maximum diameter) is produced within the filleted lead-in. In FIG. 4C, the fiber plastic coating 170 and glass cladding 180 are depicted after being chamfered and slightly offset from the chamfering (conical bore portion) surface 190. The die 130 may be (optionally removably) mounted within an axial recess of a hand tool similar to that depicted in FIG. 2.

Figure 5:
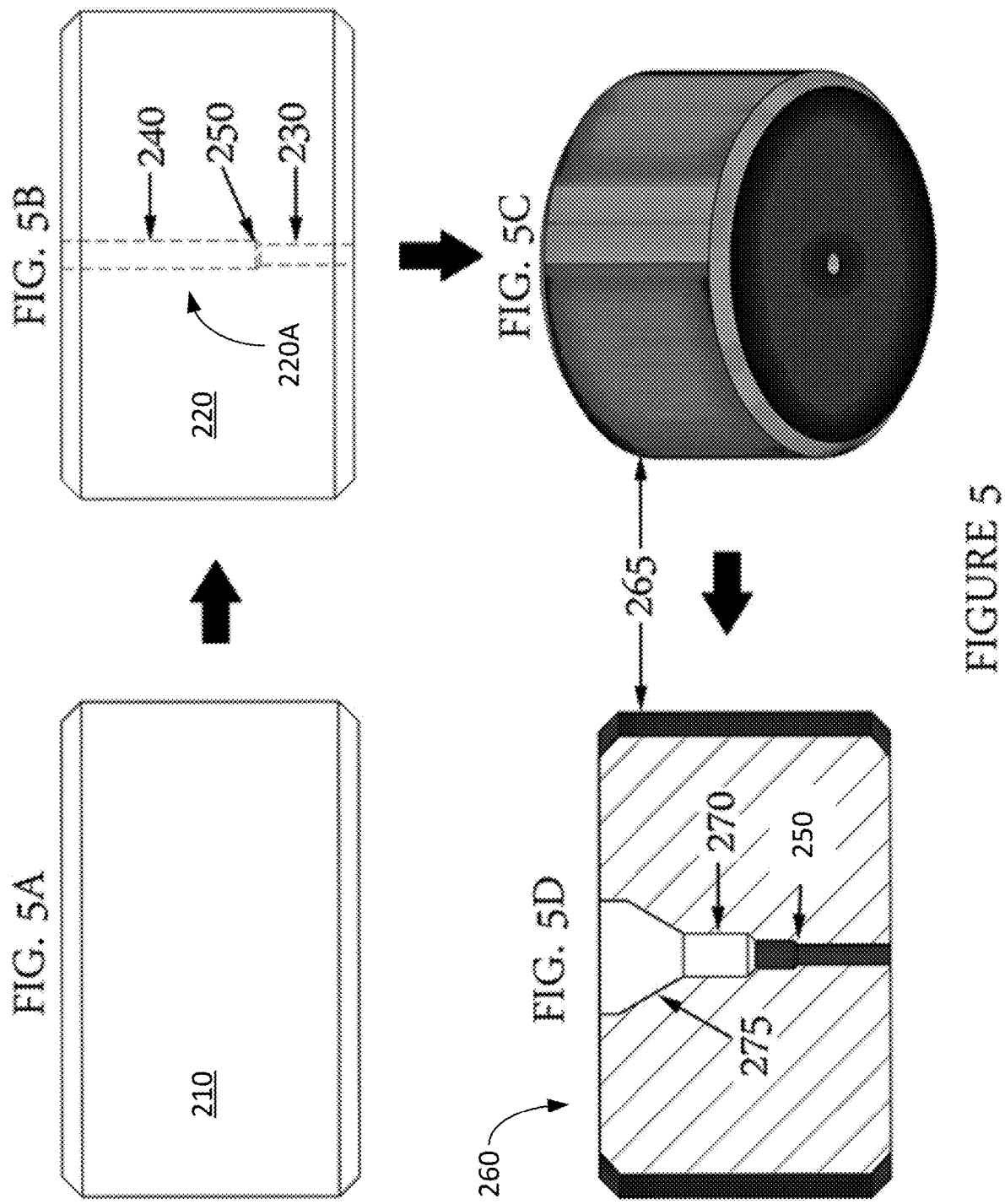
FIG. 5 (with sub-FIGS. 5A, 5B, 5C, 5D) provides a scheme for constructing a low-cost chamfering die such as that of FIG. 3. Here.

FIG. 5 illustrates production steps for fabricating a fiber chamfering die similar to the embodiment of the die 90 depicted in FIG. 3. Here, FIG. 5A shows an example of a beveled metallic (for example, aluminum) cylindrical body 210 (shown to be dimensioned as a right cylinder) that is about 5 mm in diameter and 3 mm in height. At a production step shown FIG. 5B, the aluminum cylinder 210 has been equipped with precisely-dimensioned throughout multi-sectional bore 220A (a bore portion 230 slightly larger in size than a 200 μm fiber's core maximum dimension and a bore portion 240 slightly larger than the fiber coating dimensions, in reference to critical dimensions summarized in Table 1). A substantially conical chamfering surface 250 is present to join the two bore portions, to produce a contraption 220. FIG. 5C illustrates the modified aluminum cylinder 260 after thin-film anodization 265 (illustrated with a dark shade). FIG. 5D depicts a modified die 260 now having a counterbore 270 and beveled fiber lead-in section 275 formed in the throughout bore 220A post anodization that left the fiber chamfer surface 250 anodized. (Carrying out the process of boring the fiber lead-in section 275 after the anodization procedure has been completed reduces the risk of inadvertently imparting damage to the inserted portion of the fiber that is not involved in centering the fiber.)

Figure 6:
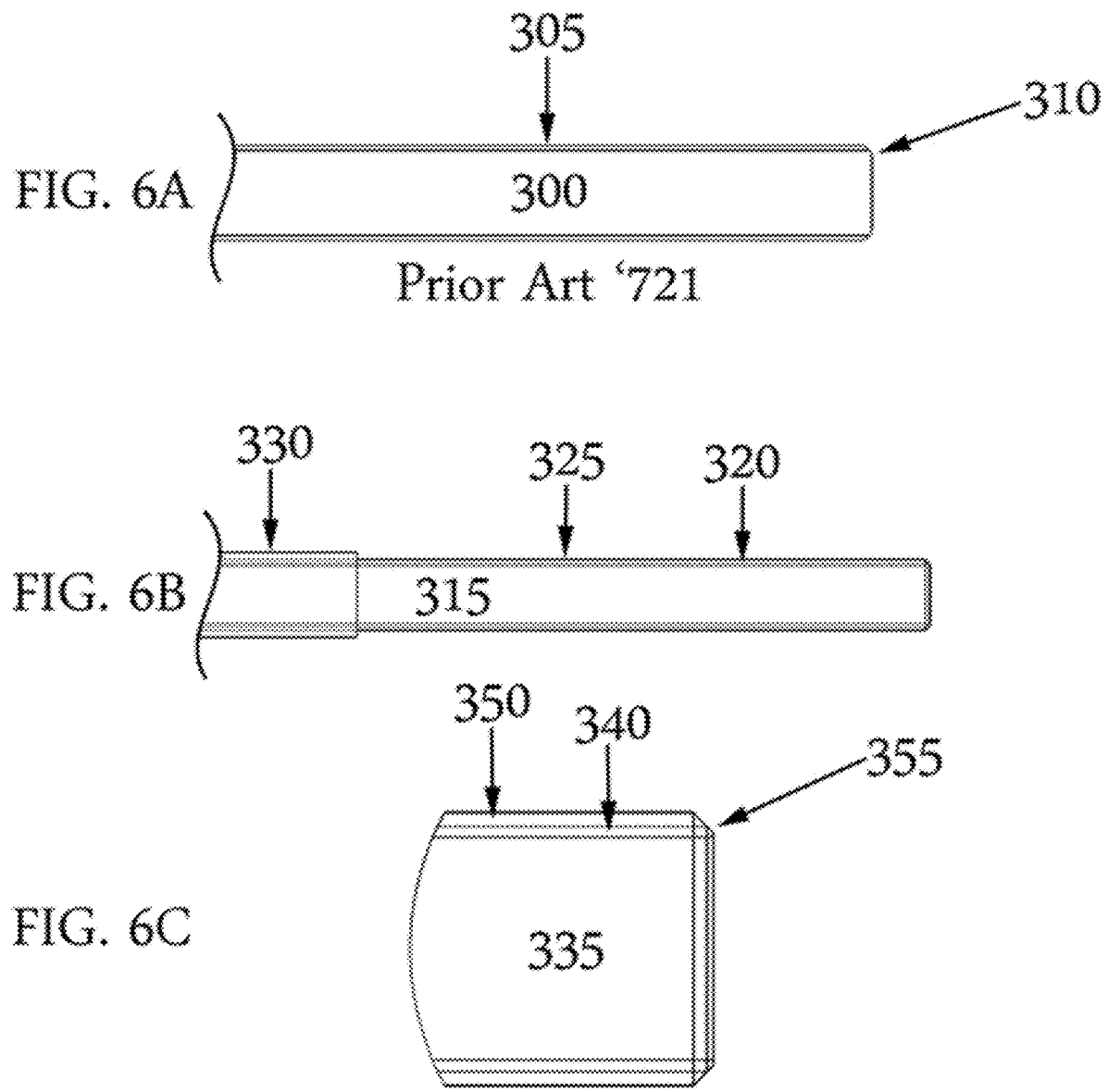
FIG. 6 (with sub-FIGS. 6A, 6B, and 6C) presents a side view of a fiber thermally "chamfered" according to the method of related art (FIG. 6A) in comparison with a side view (FIG. 6B) of the fiber formatted with the use of an embodiment of a chamfering tool structured according to an embodiment of the present invention.

FIG. 6A is a depiction of a "chamfered fiber" from prior art where the fiber core 300 and cladding 305 are melted by one of various means to fillet 310 the sharp edge that results from cleaving (which operation in this case is carried out to make the filleted end of the fiber pass through plastic tubes used in DNA/RNA cassettes or small diameter catheters). Notably, as is recognized in the art, the filleting 310 invariably extends through the glass cladding 305 and well into the fiber core 300. While filleting of the optical fiber with the use of a laser could be theoretically performed without extending the surface curvature of the fillet into the fiber core, maintaining a perfectly flat output fiber facet (required for proper operation of the surgical fiber) is substantially difficult when using thermal methods.

FIG. 6B and details of FIG. 6C reproduce the fiber tip of FIG. 4 (chamfered with the use of the embodiment of the invention) for direct comparison with that of the related art. FIG. 6B presents the fiber core 315 with glass cladding 320 with the plastic coating (aka hard polymer cladding) 325 intact, but with the thick polymer coating 330 being stripped away. The fiber tip FIG. 6C details show that the chamfer 355 only affects and reshape the glass coating layer 350 and glass cladding layer 340 of the fiber while preserving the fiber core 335 with the flat, snap-cut output face (surface).

FIG. 7 illustrates, in side and top views, an embodiment of a universal chamfering tool dimensioned such as to allow smaller-diameter optical fibers pass freely through the chamfering tool segments dimensioned to accommodate and/or chamfer the larger-diameter fibers. For orientation, the insertion or input side 33A of the die is "up" or out of the page in the top view of FIG. 7B (and corresponds to the front, distal facet of the die 10 that is facing away from the end 24B in FIG. 2A) while the output side 33B corresponds to that facet of the die 10 of FIG. 2A that is inserted into the axial recess 32. The view from the side 99 is shown in FIG. 7A.

The multi-sectional bore 77 (that includes multiple neighboring substantially cylindrical sections interconnected with one another with corresponding substantially conical section) is dimensioned such that a nominally 200 μm core fiber, for example, would pass down through the 910 μm fiber centering bore 91 and the nominally 910 μm fiber-chamfering surface 91' immediately below, through the nominally 910 μm fiber chamfer stop bore 94 and associated non-tool chamfer 84, into the nominally 550 μm fiber centering bore 55 and the 550 μm fiber chamfering surface 55' immediately below, into the nominally 550 μm fiber chamfer stop bore 54 and associated non-tool chamfer 44, then into the nominally 365 μm fiber centering bore 36 and the 365 μm fiber-chamfering surface 36' immediately below, into the nominally 273 μm centering bore 27 that serves a dual role as the 365 μm fiber stop bore and through the nominally 273 μm fiber chamfering surface 27' immediately below that, and finally into the 200 μm fiber-centering bore 2 that is dimensioned to serve a dual role (as the 273 μm fiber stop bore with its 200 μm fiber chamfering surface 2' and the 200 μm fiber stop bore 1). Surgical fibers of larger standard dimensions, when inserted into the bore 77 from the input side 33A, will pass through those sections of the bore 77 that are dimensioned to not restrict such fibers until being eventually brought into contact with a chamfering surface (of the chamfering surfaces 91', 55', 36', 27') of appropriate dimensions.

FIG. 8 (with sub-FIGS. 8A and 8B) illustrates a related embodiment of the chamfering die body that has a conical procession leading to a first centering cylindrical section of a multi-sectional bore. In one example (see FIG. 8A), the chamfering tool includes a chamfering body 80 defining a multisectional bore 82 that is centrosymmetric about a longitudinal axis 83. The bore 82 can be formatted to include a centering section 84 (FIG. 8B) adjacent to a conical chamfer section 85, which is adjacent to a substantially cylindrical outflow section 86. Notably, the centering section 84 can include a centering surface 87 and a centering diameter 88. The chamfer section 85 includes a chamfer surface 89 formed at a chamfer angle θ 90. Here, the chamfer angle is defined with respect to the longitudinal axis 83 and, as such, represents the opening angle of the conical section 85. The outflow section 86 includes an outflow surface 86A and an outflow diameter 86B.

It will be appreciated by a skilled person that—and substantially in any implementation of the body of the die of the chamfering tool—the chamfering body 10, 80, 210 may be composed of or include alumina, aluminum, tungsten carbide, stainless steel, and/or titanium. In one preferred example, the chamfering body comprises alumina. In another related example, the chamfering body comprises aluminum while the chamfering surface (89, 250, 55' etc) may comprise anodized aluminum. In another instance, the chamfering body can be held within a support composed of the same or different composition as the chamfering body (see e.g., FIG. 2A, 2B).

Generally, (an internal) surface of the bore formed throughout the die body of and embodiment of the tool can be composed of any of alumina, zirconia, diamond, tungsten carbide, titanium dioxide, boron nitride, boron carbide, and/or a silicon carbide. In another example, the bore surface is composed of a material with hardness greater than the hardness of the target fiber core. In one example, the chamfering (conical) surface is defined by alumina, zirconia, diamond, tungsten carbide, titanium dioxide, boron nitride, boron carbide, and/or silicon carbide. Alternatively or in addition to the choice of any of the above-mentioned materials, the chamfering (conical) surface of the bore can be formatted to have a surface hardness of at least 20 GPa (which is defined, again, with respect to a smaller hardness of a typical optical fiber glass). In yet another related example, the centering surface (for example, surface 87 of FIG. 8A) can be configured to have a roughness average (Ra) of less than about 0.025 about 0.05 about 0.75 about 0.1 about 0.15 or about 0.2 μm; preferably less than about 0.025 about 0.05 about 0.75 or about 0.1 μm—that is, within the range of surface roughnesses which, when brought in contact with the glass of the optical fiber during the chamfering procedure, prevent the optical fiber from chipping at an edge of its output facet. In still another related example, the chamfering surface can be configured to have a figured of a roughness average that is greater than that of the centering surface (such as surface 87).

While the dimensionality of a multi-sectional bore through the die body has been already alluded to above, the skilled person will readily appreciate that at least in one implementation a diameter of a substantially cylindrical centering portion of the bore (referred to as a centering diameter) is necessarily selected to correspond to the nominal diameter of a corresponding target optical fiber. The five standard surgical optical fibers have nominal diameters of 200, 273, 365, 550 and 910 μm. In reference to an embodiment of FIG. 7, for example, in at least one implementation of such embodiment the multi-sectional bore 77 is made to necessarily include at least two centering diameters selected from about 285 to 295 μm for a 200 μm fiber; about 340 μm to 350 μm for a 273 μm fiber; about 445 to 455 μm for a 365 μm fiber; about 645 μm to 655 μm for a 550 μm fiber; and about 1055 to 1075 μm for a 910 μm fiber.

In at least one instance, the chamfering body defines a plurality of bores that are individually centrosymmetric about a chosen longitudinal axis; each bore including an centering section (e.g., 36) adjacent to a chamfer section (e.g., 36') which is adjacent to an outflow section (e.g., 27); each centering section including a centering surface and a centering diameter; each chamfer section including a chamfer surface and a chamfer angle; each outflow section including an outflow surface and an outflow diameter. In this instance, each bore can have a centering diameter selected from about 285 μm to 295 μm for a 200 μm fiber; about 340 μm to 350 μm for a 273 μm fiber; about 445 μm to 455 μm for a 365 μm fiber; about 645 μm to 655 μm for a 550 μm fiber; and about 1055 μm to 1075 μm for a 910 μm fiber. By way of example, FIG. 7A depicts a chamfering tool having a single bore with a plurality of axially symmetric chamfering regions/sections. In one example, chamfering regions can overlap; for example, the tool can include a first region and a second region, for example for a 200 μm fiber and a 273 μm fiber, respectively. In this example, the first region includes an outflow section 2, a chamfer surface 27', and a centering section 27; the second region includes an outflow section 27 which overlaps with or is identical to the first region's centering section, a chamfer surface 36', and a centering section 36. In another example, the chamfering regions can be separated by a reducing chamfer; for example, the first region includes an outflow section 54, a chamfer surface 55', and a centering section 55; the second region includes an outflow section 94, a chamfer surface 91', and a centering section 91. These two regions are separated by a reducing chamfer 84. In still another example, the tool can include a plurality of regions wherein first and second regions have centering and outflow regions that overlap and wherein a third region is divided from another region (e.g., the second region or a fourth region) by a reducing chamfer.

In another instance, the chamfer angle is about 23° to about 68°, preferably about 34° to about 56°. In a preferred case, the chamfer angle is about 45°±5°.

In yet another instance, the outflow section can include an outflow diameter that is approximately equal to or slightly larger than the nominal fiber diameter. In one example, the outflow diameter can be selected from about 210 μm to 220 μm for a 200 μm fiber; about 285 μm to 295 μm for a 273 μm fiber; about 375 μm to 385 μm for a 365 μm fiber; about 565 μm to 575 μm for a 550 μm fiber; and about 945 μm to 960 μm for a 910 μm fiber. In another example, the outflow diameter is about 10 μm to about 50 μm greater than a nominal fiber diameter, preferably, about 10 μm to about 35 μm greater than a nominal fiber diameter.

It is appreciated that a process of using the above-described chamfering tool to form a chamfer on the target cleaved optical fiber includes positioning the chamfering tool in a hand of the user such that the proximal portion of the bar-like body of the tool is in contact with and supported by the palm of the hand and/or while its distal portion is squeezed between two fingers (for example, the thumb and the index finger); inserting the cleaved end of the optical fiber into the bore of the die of the tool, removably affixed in the axial recess at the distal end of the body of the tool, and moving this cleaved end through a first cylindrical portion of the bore (that has a diameter larger than an outer glass cladding diameter of the fiber) and along a cylindrical portion of the bore (that has a diameter smaller than the outer glass cladding diameter but larger than a diameter of the glass core of the fiber) to form contact between the cleaved end and a surface of the conical portion. Then, by rotating the optical fiber about the axis in contact with and with respect to the conical portion, forming a chamfer only at the glass cladding of the optical fiber while preventing the glass core from being chamfered due to a dimensional mismatch between a diameter of the conical portion and the diameter of the glass core, thereby confining the chamfered surface to the glass cladding at the cleaved end. The so-chamfered surface is then removed from the bore. When the target fiber is changed—for example, from a first standard surgical optical fiber of one conventionally-recognized size to a second standard surgical optical fiber of another conventionally-recognized size, intraoperatively for example—the user may replace the die (in case the die installed in the tool at the time has a bore with dimensions not corresponding to those of the second fiber) or possibly re-used the same die in case when the bore of the die is multi-sectional and includes a cylindrical section and an immediately adjacent conical section dimensionally-accommodating the second fiber. In the latter case, the operation described above is substantially repeated, while in the former case the die is replaced with a die containing a bore with dimensions corresponding to dimensions of the second fiber, removably affixed in the body of the tool, after which the chamfering process is repeated. Notably, rotating the tool with the die about its axis with fingers while the tool is supported in the hand does not require any action to be performed at the distal end of the fiber which—in the case of surgical optical fiber—may then remain attached to the laser source used during the surgical procedure.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself. The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

The invention claimed is:

1. A tool comprising:
    a die with a bore within the die, the bore having a first axis and
        a first cylindrical portion with a first diameter,
        a second cylindrical portion having a second diameter that is smaller than the first diameter, and
        a first conical portion including a first base that has the first diameter and a second base that has the second diameter, said first conical portion connecting the first and second cylindrical portions, and
    a housing body shaped as a bar having distal and proximal ends, a second axis, and an axial recess dimensioned to fixate at least a portion of the die therein when the first and second axes substantially coincide,
    wherein a surface of the first conical portion possesses at least one of
        (1a) a first hardness that is greater than a second hardness of a glass material, and
        (1b) a first averaged surface roughness that is greater than a second averaged surface roughness of a surface of any of the first and second cylindrical surfaces, and
    wherein the tool is configured to chamfer an optical fiber.

2. The tool according to claim 1, wherein the housing body includes a distal portion having a knurled outer surface, and a proximal portion axially connected to the distal portion and having a terminus dimensioned to have a larger first cross-sectional dimension than a second cross-sectional dimension of the proximal portion, wherein the first and second cross-sectional dimensions are defined in a plane transverse to the first axis.

3. The tool according to claim 2, wherein at least one of the following conditions is satisfied:
    (3a) the housing body further includes a handle portion extending along the second axis and coupling the proximal portion to the distal portion; and
    (3b) an outer surface of the terminus us a convex surface.

4. The tool according to claim 1, wherein said axial recess is formed at the distal end with an open end of the recess facing away from the proximal end.

5. The tool according to claim 1, wherein a cross-section of the axial recess that is transverse to the second axis has a substantially elliptical perimeter.

6. The tool according to claim 1, wherein at least one of the following conditions is satisfied:
    (7a) the die has an outer surface dimensioned as elliptic cylindrical surface;
    (7b) said outer surface of the die is rotationally-symmetric about the first axis;
    (7c) said outer surface of the die carries a thread thereon;
    (7d) the axial recess is axially-symmetric about the first axis; and
    (7e) the axial recess is dimensioned to fixate said at least a portion of the die therein removably.

7. The tool according to claim 1, further comprising a fastener cooperated with the housing body at the distal end and configured to affix the die in the axial recess while the first and second axes substantially coincide.

8. The tool according to claim 1, wherein the bore extends throughout the die to provide a fluid communication between a first portion of an ambient space next to a first surface of the die and a second portion of the ambient space next to a second surface of the body,
    wherein each of the first and second surfaces of the die is transverse the first axis.

9. The tool according to claim 1, wherein the bore further comprises:
   a second conical portion including a third base that has the second diameter and a fourth base that has a third diameter that is smaller than the second diameter, said second conical portion being connected to the second cylindrical portion.

10. The tool according to claim 9, wherein the bore further comprises
    a third cylindrical portion axially connected to the second conical portion and having the third diameter.

11. The tool according to claim 1, wherein the optical fiber includes a glass core with a glass core diameter, a glass cladding with a glass cladding diameter, and wherein the die is dimensioned to have the first diameter to be larger than the glass cladding diameter, the second diameter is smaller than the glass cladding diameter and larger than the glass core diameter.

12. The tool according to claim 1, wherein the first hardness is at least 20 GPa.

13. The tool according to claim 1, wherein the surface of the first conical portion carries a coating thereon, said coating having the at least one of the first hardness and the first averaged roughness.

* * * * *